United States Patent
Agarwal et al.

(10) Patent No.: US 10,624,566 B2
(45) Date of Patent: Apr. 21, 2020

(54) 3D ISOTROPIC MICROSCALE METAMATERIALS AND METHODS OF MANUFACTURE

(71) Applicant: Regents of the University of Minnesota, Minneapolis, MN (US)

(72) Inventors: Kriti Agarwal, Uttar Pradesh (IN); Chao Liu, Heilongjiang (CN); Jeong-Hyun Cho, Woodbury, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/997,604

(22) Filed: Jun. 4, 2018

(65) Prior Publication Data

US 2018/0360354 A1    Dec. 20, 2018

Related U.S. Application Data

(60) Provisional application No. 62/514,212, filed on Jun. 2, 2017.

(51) Int. Cl.
| | | |
|---|---|---|
| *A61B 5/1468* | (2006.01) | |
| *C01B 32/198* | (2017.01) | |
| *H01P 7/00* | (2006.01) | |
| *H01Q 15/00* | (2006.01) | |
| *A61B 5/145* | (2006.01) | |

(52) U.S. Cl.
CPC ........ *A61B 5/1468* (2013.01); *A61B 5/14532* (2013.01); *C01B 32/198* (2017.08); *H01P 7/00* (2013.01); *H01Q 15/0086* (2013.01); *A61B 2562/02* (2013.01); *A61B 2562/12* (2013.01); *C01B 2204/22* (2013.01)

(58) Field of Classification Search
CPC .............. A61B 5/1468; A61B 5/14532; A61B 2562/02; A61B 2562/12; C01B 32/198; C01B 2204/22; H01P 7/00; H01Q 15/0086
USPC ......................................................... 333/219
See application file for complete search history.

(56) References Cited

U.S. PATENT DOCUMENTS

| 9,408,564 B2 | 8/2016 | Porch et al. |
| 2008/0200790 A1 | 8/2008 | Kim et al. |
| 2012/0135237 A1 | 5/2012 | Gracias et al. |

OTHER PUBLICATIONS

Appavoo et al., "Detecting Nanoscale Size Dependence in VO2 Phase Transition Using a Split-Ring Resonator Metamaterial", Nano Lett. 2011, 11, pp. 1025-1031 (Year: 2011).*

(Continued)

*Primary Examiner* — Benny T Lee
*Assistant Examiner* — Hafizur Rahman
(74) *Attorney, Agent, or Firm* — Dicke, Billig & Czaja, PLLC

(57) ABSTRACT

3D microscale metamaterial structures and methods of making. The metamaterial structure includes a polygonal structure having a plurality of panels connected to one another at structure corners. A metal resonator pattern is provided on each of the panels. The resonator patterns of neighboring panels are electromagnetically coupled to one another across a gap between the resonator patterns at the corresponding structure corner. The panels can be a polymer material, layers of graphene oxide, etc. The metamaterial structure can be a 3D octagram split-ring resonator, and is completely isotropic. The 3D metamaterial structure can be made by a self-folding process.

20 Claims, 12 Drawing Sheets

(56) References Cited

OTHER PUBLICATIONS

Burckel et al., "Coupling effects in dense arrays of 3D optical metamaterials" Proc. SPIE 10719, Metamaterials,Metadevices, and Metasystems 2018 (Year: 2018).*

Domingos, I.D., "Nickel nanowire synthesis for next-generation transparent conductors", Universidade Nova De Lisboa, Sep. 2016 (Year: 2016).*

Burckel et al. "Multilayer infrared metamaterial fabrication using membrane projection lithography", published Nov. 11, 2011, J. Vac. Sci. Technol. B 29(6), Nov./Dec. 2011 (Year: 2011).*

Liu et al., "Folding 2D Structures into 3D Configurations at the Micro/Nanoscale: Principles, Techniques, and Applications", Adv. Mater. 2019, 31, 1802211, 2018 WILEY-VCH Verlag GmbH & Co. KGaA, Weinheim, pp. 1-20 (Year: 2018).*

Gracias, "Three dimensional self-assembly at the nanoscale", Proc. of SPIE vol. 8750, pp. 87500O-1-12, © 2013 SPIE (Year: 2013).*

Cheng et al., "Broadband 3D isotropic negative-index metamaterial based on fishnet structure", Eur. Phys. J. B (2012) 85, pp. 1-6 (Year: 2012).*

Li et al., "Three-dimensional graphene architectures", Nanoscale, published on Jul. 26, 2012, pp. 5549-5563 (Year: 2012).*

Gracias et al. "Self-Folding Thin-Film Materials: From Nanopolyhedra to Graphene Origami", vol. 37, Issue Sep. 9, 2012, pp. 847-854, Materials Research Society 2012 (Year: 2012).*

Parida et al., "Characterization of Optical Properties of SU-8 and Fabrication of Optical Components", ICOP 2009-International Conference on Optics and Photonics CSIO, Chandigarh, India, Oct. 30-Nov. 1, 2009 (Year: 2009).*

Mazhorova, A.; Markov, A.; Ng, A.; Chinnappan, R.; Skorobogata, O.; Zourob, M.; Skorobogatiy, M. Label-free bacteria detection using evanescent mode of a suspended core terahertz fiber. Opt. Express 2012, 20, 5344-5355.

Rea, I.; Lamberti, A.; Rendina, I.; Coppola, G.; Gioffré, M.; Iodice, M.; Casalino, M.; De Tommasi, E.; De Stefano, L. Fabrication and characterization of a porous silicon based microarray for label-free optical monitoring of biomolecular interactions. J. Appl. Phys. 2010, 107, 014513.

Wu, X.; Yiwen, E.; Xu, X.; Wang, L. Label-free monitoring of interaction between DNA and oxaliplatin in aqueous solution by terahertz spectroscopy. Appl. Phys. Lett. 2012, 101, 033704.

Yeh, K.; Hebling, J.; Hoffmann, M. C.; Nelson, K. A. Generation of high average power 1kHz shaped THz pulses via optical rectification. Opt. Commun. 2008, 281, 3567-3570.

Carr, G. L.; Martin, M. C.; McKinney, W. R.; Jordan, K.; Neil, G. R.; Williams, G. P. High-power terahertz radiation from relativistic electrons. Nature 2002, 420, 153-156.

Yang, Y.; Mandehgar, M.; Grischkowsky, D. R. Understanding THz pulse propagation in the atmosphere. IEEE Trans. Terahertz Sci. Technol. 2012, 2, 406-415.

Guerboukha, H.; Yan, G.; Skorobogata, O.; Skorobogatiy, M. Silk foam terahertz waveguides. Adv. Opt. Mater. 2014, 2, 1181-1192.

Nagel, M.; Meyer, C.; Heiliger, H.; Dekorsy, T.; Kurz, H.; Hey, R.; Ploog, K. Optical second-harmonic probe for ultra-high frequency on-chip interconnects with benzocyclobutene. Appl. Phys. Lett. 1998, 72, 1018-1020.

Nagel, M.; Richter, F.; Haring-Bolivar, P.; Kurz, H. A functionalized THz sensor for marker-free DNA analysis. Phys. Med. Biol. 2003, 48, 3625.

Byrne, M.; Cunningham, J.; Tych, K.; Burnett, A.; Stringer, M.; Wood, C.; Dazhang, L.; Lachab, M.; Linfield, E.; Davies, A. Terahertz vibrational absorption spectroscopy using microstrip-line waveguides. Appl. Phys. Lett. 2008, 93, 182904.

Rodriguez-Ulibarri, P.; Beruete, M. Sensing at Terahertz Frequencies. In Fiber Optic Sensors; Matias, I. R., Ikezawa, S., Corres, J., Eds.; Springer International Publishing: Switzerland, 2017; vol. 21, pp. 301-327.

Hasebe, T.; Kawabe, S.; Matsui, H.; Tabata, H. Metallic mesh-based terahertz biosensing of single-and double-stranded DNA. J. Appl. Phys. 2012, 112, 094702.

Yoshida, H.; Ogawa, Y.; Kawai, Y.; Hayashi, S.; Hayashi, A.; Otani, C.; Kato, E.; Miyamaru, F.; Kawase, K. Terahertz sensing method for protein detection using a thin metallic mesh. Appl. Phys. Lett. 2007, 91, 253901.

Chen, T.; Li, S.; Sun, H. Metamaterials application in sensing. Sensors 2012, 12, 2742-2765.

Liu, C.; Agarwal, K.; Zhang, Y.; Chowdhury, D. R.; Azad, A. K; Cho, J. Displacement Current Mediated Resonances in Terahertz Metamaterials. Adv. Opt. Mater. 2016, 4, 1302-1309.

Park, S.; Hong, J.; Choi, S.; Kim, H.; Park, W.; Han, S.; Park, J.; Lee, S.; Kim, D.; Ahn, Y. Detection of microorganisms using terahertz metamaterials. Sci. Rep. 2014, 4.

Wellenzohn, M.; Brandl, M. A theoretical design of a biosensor device based on split ring resonators for operation in the microwave regime. Procedia Eng. 2015, 120, 865-869.

Xu, X.; Peng, B.; Li, D.; Zhang, J.; Wong, L. M.; Zhang, Q.; Wang, S.; Xiong, Q. Flexible visible—infrared metamaterials and their applications in highly sensitive chemical and biological sensing. Nano Lett. 2011, 11, 3232-3238.

Melik, R.; Unal, E.; Perkgoz, N. K.; Puttlitz, C.; Demir, H. V. Flexible metamaterials for wireless strain sensing. Appl. Phys. Lett. 2009, 95, 181105.

Rusni, I. M.; Ismail, A.; Alhawari, A. R. H.; Hamidon, M. N.; Yusof, N. A. An aligned-gap and centered-gap rectangular multiple split ring resonator for dielectric sensing applications. Sensors 2014, 14, 13134-13148.

Horestani, A. K.; Fumeaux, C.; Al-Sarawi, S. F.; Abbott, D. Displacement sensor based on diamond-shaped tapered split ring resonator. Sensors Journal, IEEE 2013, 13, 1153-1160.

Fischer, B.; Walther, M.; Jepsen, P. U. Far-infrared vibrational modes of DNA components studied by terahertz time-domain spectroscopy. Phys. Med. Biol. 2002, 47, 3807.

Liu, X.; MacNaughton, S.; Shrekenhamer, D. B.; Tao, H.; Selvarasah, S.; Totachawattana, A.; Averitt, R. D.; Dokmeci, M. R.; Sonkusale, S.; Padilla, W. J. Metamaterials on parylene thin film substrates: Design, fabrication, and characterization at terahertz frequency. Appl. Phys. Lett. 2010, 96, 011906.

Chen, C.; Ishikawa, A.; Tang, Y.; Shiao, M.; Tsai, D. P.; Tanaka, T. Uniaxial-isotropic Metamaterials by Three-Dimensional Split-Ring Resonators. Adv. Opt. Mater. 2015, 3, 44-48.

Koschny, T.; Zhang, L.; Soukoulis, C. Isotropic three-dimensional left-handed metamaterials. Phys. Rev. B 2005, 71, 121103.

Baena, J.; Jelinek, L.; Marques, R.; Mock, J.; Gollub, J.; Smith, D. Isotropic frequency selective surfaces made of cubic resonators. Appl. Phys. Lett. 2007, 91, 191105.

Baena, J.; Jelinek, L.; Marques, R.; Zehentner, J. Electrically small isotropic three-dimensional magnetic resonators for metamaterial design. Appl. Phys. Lett. 2006, 88, 134108.

Joung, D.; Gu, T.; Cho, J. Tunable Optical Transparency in Self-Assembled Three-Dimensional Polyhedral Graphene Oxide. ACS nano 2016, 10, 9586-9594.

Cho, J.; Keung, M.D.; Verellen, N.; Lagae, L.; Moshchalkov, V. V.; Van Dorpe, P.; Gracias, D. H. Nanoscale origami for 3D optics. Small 2011, 7, 1943-1948.

Cho, J.; Gracias, D. H. Self-assembly of lithographically patterned nanoparticles. Nano Lett. 2009, 9, 4049-4052.

Cho, J.; Hu, S.; Gracias, D. Self-assembly of orthogonal three-axis sensors. Appl. Phys. Lett. 2008, 93, 043505.

Joung, D.; Agarwal, K.; Park, H.; Liu, C.; Oh, S.; Cho, J. Self-Assembled Multifunctional 3D Microdevices. Adv. Electron. Mater. 2016, 2: 1500459.

Agarwal, K. Three-Dimensional Anisotropic Metamaterials as Triaxial Optical Inclinometers.

Vanexter, M.; Fattinger, C.; Grischkowsky, D. Opt. Lett. 1989, 14 (20), 1128-1130.

Wu, Q.; Litz, M.; Zhang, X. C. Appl. Phys. Lett. 1996, 68 (21), 2924-2926.

Park, H.-R.; Ahn, K. J.; Han, S.; Bahk, Y.-M.; Park, N.; Kim, D.-S. Nano Lett. 2013, 13, 1782-1786.

Gusev, S.; Borovkova, M.; Strepitov, M.; Khodzitsky, M. Blood optical properties at various glucose level values in THz frequency range. Proc. SPIE 2015, 9537, 95372A.

(56) References Cited

OTHER PUBLICATIONS

Cherkasova, O.; Nazarov, M.; Shkurinov, A. In the investigation of blood and skin THz response at high glucose concentration, Proceedings of the 40th International Conference on Infrared, Millimeter, and Terahertz waves, Hong Kong, Aug. 23-28, 2015; IEEE: New York, 2015.

Topsakal, E.; Karacolak, T.; Moreland, E. C. In Glucose-dependent dielectric properties of blood plasma, URSI General Assembly and Scientific Symposium, Istanbul, Turkey, Aug. 13-20, 2011; IEEE: New York, 2011.

Karacolak, T.; Moreland, E. C.; Topsakal, E. Cole-cole model for glucose-dependent dielectric properties of blood plasma for continuous glucose monitoring. Microw. Opt. Technol. Lett. 2013, 55, 1160-1164.

J.R. Wendt et al., "Fabrication techniques for three-dimensional metamaterials in the midinfrared", J.Vac.Sci.Technol. B 28(6), Nov./Dec. 2010, C6O30-C6O33.

X.Y.Liu, "A Miniaturized CSRR Loaded Wide-Beamwidth Circularly Polarized Implantable Antenna for Subcutaneous Real-Time Glucose Monitoring", IEEE Antennas and Wireless Propagation Letters, 2017.

H. Tao, "Metamaterials on Paper as a Sensing Platform", Advanced Materials, 2011.

H. Chen et al., "Manipulation of terahertz radiation using metamaterials", Laser & Photonics Reviews, 5, No. 4, 513-533 (2011).

H. Chen et al., "Complementary planar terahertz metamaterials", Optics Express, Feb. 5, 2007, vol. 15, No. 3, p. 1084-1095.

W. J. Padilla et al., "Electrically resonant terahertz metamaterials: Theoretical and experimental investigations", Physical Review B 75, 041102(R) (2007).

\* cited by examiner

3D ISOTROPIC MICROSCALE METAMATERIALS AND METHODS OF MANUFACTURE

CROSS-REFERENCE TO RELATED APPLICATIONS

This Non-Provisional Patent Application claims the benefit of the filing date of U.S. Provisional Patent Application Ser. No. 62/514,212, filed Jun. 2, 2017, the entire teachings of which are incorporated herein by reference.

STATEMENT REGARDING FEDERALLY SPONSORED RESEARCH OR DEVELOPMENT

This invention was made with government support under CMMI 1454293 awarded by the National Science Foundation. The government has certain rights in this invention.

BACKGROUND

The present disclosure relates to microscale metamaterials useful, for examples, as sensors. More particularly, it relates to microscale metamaterials exhibiting isotropic properties, and methods of manufacturing the same.

Terahertz (THz) spectroscopy has emerged as an attractive avenue for label-free, fast and versatile detection of chemical and biological substances. Recently, development of high power and long propagation length THz sources has promoted its use for free-space spectroscopy, microstrip line, and metallic mesh methods for the analysis of the biomaterials. Sensors based on the free-space spectroscopy measure changes in dielectric constant due to binding of the molecules. However, this method requires large quantities of the sample materials in order to achieve a reliable response. Microstrip line-based sensors overcome the need for large sample quantities. But, the stronger electric field confinement exists only between the substrate and the strip line, decaying severely in the air region above the strip line. This decay limits the sensitivity of the structure since the high field confinement area is inaccessible to the targeted molecules. Another type of sensors, a metallic mesh based structure, benefits from strong localization of the electromagnetic field at the openings of the mesh and operates by sensing changes in the refractive index near the surface of the metal-air interface. However, the frequency response for these structures resembles that of a high pass filter (no narrow peak exists) with a very low signal transduced at low concentrations of the target molecules. Thus, for higher sensitivity detections, it is necessary to leverage structures that induce a strong coupling between the incident electromagnetic wave and the resonators to deliver sharp edges in the transmission response and create a high field confinement area for detection of the targeted material.

Metamaterials (MMs) are artificial materials that can create unique physical and optical properties unseen in natural materials and that renders them suitable for various applications in sensors, optical devices, plasmonic devices, etc. Terahertz metamaterials (THz MMs) are good candidates as sensors for the detection of chemicals and biomaterials, temperature, strain, alignment, and position. Spli-tring resonator (SRR)-based metamaterial structures have been extensively studied because of the behavior of relatively sharp edges as well as their ability to manipulate electromagnetic waves and strong confinement of the magnetic field (H) within the arms of the resonator and the electric field (E) confinement within the split. The split contributes capacitance to the resonance frequency which is directly proportional to the relative permittivity. The confinement of electric field within the capacitance controlling split make it a hotspot that has a higher sensitivity than the surrounding areas where the electric field is much weaker. Hence, when a SRR is exposed to a biomolecule, a large change in resonance frequency is seen as a function of the relative permittivity of the external molecule near the split.

The dependence of the resonance frequency on the aforementioned parameters has allowed SRRs to be used in a wide range of sensors to detect micro-organisms, strain, dielectric constants, and displacement without the effects of ambient temperature and pressure. Especially, THz SRR-based biosensors offer an attractive avenue for the development of small scale, label-free detectors capable of being introduced orally or intravenously because of their microscale dimensions, which are comparable to that of most micro-organisms, and the non-ionizing effects of the THz radiation.

However, the polarization dependence of a split-ring resonator (SRR) transmission response poses a drawback. When the magnetic field is polarized perpendicular to the split-containing arm of the resonator, the structure is in $1^{st}$ mode (magnetic resonance). When the electric field is polarized perpendicular to the split-containing arm of the resonator, the structure is in $2^{nd}$ mode (electric resonance). As the SRR is rotated from 0° to 90°, the $1^{st}$ mode reduces and the $2^{nd}$ mode increases, the reverse phenomenon takes places on rotating from 90° to 180°. The transmission at $\theta=0°$ ($T_\theta$) decreases as a function of the rotation angle such that $T(\theta)=1-(1-T_\theta)*|\cos^2 \theta|$. As a result, an ambiguity in the transmission spectrum is produced, such that variation due to presence of external molecules or rotation of the SRR cannot be discerned. The angle dependent sinusoidal or anisotropic properties of the SRR design limits their application as sensors when the orientation of the resonator is difficult to control.

SUMMARY

The inventors of the present disclosure recognized that a need exists for isotropic metamaterials that overcome one or more of the above-mentioned problems.

When split-ring resonator (SRR) structures have light incident on them, a strong drop in transmission is seen at their resonance frequency. In the presence of foreign materials/particles/molecules, this resonance frequency changes according to the properties of the material it was exposed to. However, when used as a sensor for in-vivo detection, it can be difficult to maintain the angle of the resonator. Moreover, for small quantities of foreign material, we may only see a change in amplitude and not frequency. Thus, the angle dependent sinusoidal property of the C-shape poses a major challenge under both the above conditions.

Some aspects of the present disclosure are directed to a three-dimensional (3D) microscale metamaterial structure. The metamaterial structure includes a polygonal structure having at least a first panel and a second panel. An edge of the first panel is connected to an edge of the second panel at structure corner. A metal resonator pattern is provided on each of the first and second panels. In this regard, the resonator pattern carried by the first panel is electromagnetically coupled to the resonator pattern carried by the second panel across a gap between the resonator patterns at the first structure corner. In some embodiments, the polygonal structure is a cube with six of the panels and the resonator pattern provided on each of the panels is a symmetrical X shape. The gap or split at each of the structure corners of the cube is 3D, so it is equally affected by all the parameters of light (i.e. direction of propagation, electric field and magnetic field). Hence, is some non-limiting embodiments, the metamaterial structure is a 3D cube with X-shaped octagram resonator (3D star) that acts as an isotropic metamaterial that can be used for highly sensitive detection of foreign particles. The strong 3D coupling of each resonator segment to its neighbor, enhances the overall sensitivity of the octagram. The strong coupling and the use of amplitude as a marker for low concentration foreign materials can make the 3D metamaterial structure of the present disclosure to have a much higher sensitivity compared to the two-dimensional (2D) split-ring resonator-based sensors. In some embodiments, each of the panels are formed of a polymer material. In other embodiments, each of the panels includes at least two layers of graphene oxide.

Other aspects of the present disclosure are directed toward methods of making a 3D microscale metamaterial structure. The method includes forming a 2D net comprising an array of microscale panels each carrying a metal resonator pattern. Immediately adjacent ones of the panels within the array are connected by a hinge. The 2D net is caused to self-fold into a three-dimensional shape, for example by exposing the 2D net to a temperature sufficient to cause the hinges to melt. In some embodiments, the step of forming the 2D net includes depositing a polymer to generate each of the panels. In other embodiments, the step of forming the 2D net includes depositing at least two layers of graphene oxide to generate each of the panels.

DETAILED DESCRIPTION

Figure 1A:
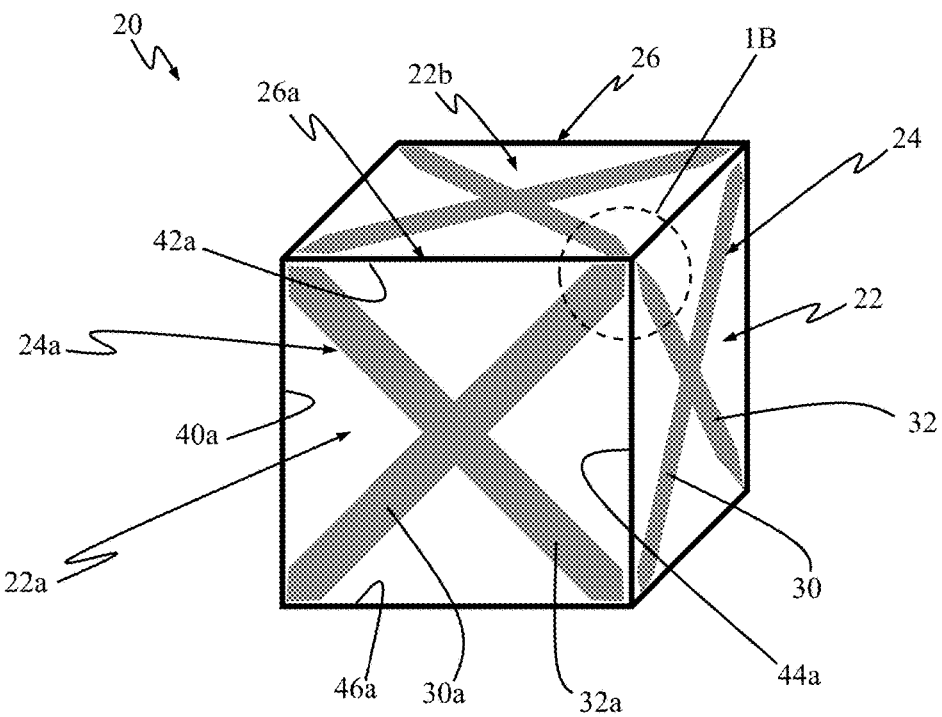
FIG. 1A is a simplified perspective view of a 3D microscale metamaterial structure in accordance with principles of the present disclosure.

One embodiment of a three-dimensional (3D), microscale metamaterial structure 20, such as a sensor structure, in accordance with principles of the present disclosure is shown in FIG. 1A. The structure 20 includes a plurality of panels 22 (three of which are visible in FIG. 1A) each supporting a resonator or resonator pattern 24. The panels 22 combine to define a hollow, 3D polygram shape (e.g., a cube), with neighboring panels 22 of the 3D shape combining to define a structure corner 26. For example, as identified in FIG. 1A, neighboring panels 22a, 22b define a structure corner 26a. The resonator patterns 24 of neighboring panels 22 are split or spaced from one another at the corresponding structure corner 26, with the resonator patterns 24 of all the panels 22 combining to define or generate a split-ring resonator (SRR) as described below. The structure 20 is considered to be a microscale structure in that the major dimension of the structure 20 in any direction is not greater than 1000 μm. In some embodiments, the panels 22 define a cubic shape, and the resonator patterns 24 collectively define a 3D octagram split-ring resonator (OSRR). The 8-pointed 3D octagram ensures uniform coupling to each of the resonator patterns 24 in all directions for any orientation. Regardless, the 3D microscale metamaterial structures of the present disclosure can be substantially isotropic (orientation invariant transmission response), within 5% of a completely isotropic structure. In other embodiments, the 3D microscale metamaterial structures of the present disclosure are completely isotropic.

In some embodiments, each of the panels 22 can have a substantially identical construction (i.e., within 5% of a truly identical construction) in terms of dimensions and materials. For example, the panels 22 can each have an identical shape (e.g., square, rectangle, triangle, etc.), with a major dimension of less than 1000 μm.

In some embodiments, each of the panels 22 is a continuous body or structure formed of a polymer material that is, for example, transparent to light. One non-limiting example of a material useful as the panels 22 is an epoxy, such as a photodefinable epoxy available from MicroChem Corp. or Newton, Mass. under the trade designation SU-8. Other polymer materials cable of supporting the corresponding resonator pattern 24 in a manner that does not interfere with use of the structure 20 as a resonator-type sensor are also acceptable.

In other embodiments, each of the panels 22 are formed of, or include, a graphene oxide (GO) material or layers (e.g., each of the panels 22 can include or consist of two or more GO layers, optionally at least five GO layers). GO is a nanomaterial with monolayer of carbon atoms and oxygen functional groups (such as epoxy, carboxyl, carbonyl, hydroxyl groups, etc.). The chemical structure of GO imparts unique properties such as amphiphilicity (i.e., hydrophobic properties from graphene structure and hydrophilic properties form the oxygen-containing functional groups), stability and high dispersibility in aqueous solutions, affinity for aromatic rings and fluorescence-quenching capabilities.

It has also been shown that GO laminates are vacuum-tight in a dry state, but when hydrated their interlayer spacing increases. The hydrated GO layer acts as a molecular sieve that does not allow molecules of radii greater than 0.45 nm to pass through it. The GO layer also demonstrates a strong adsorption for the filtered molecules onto its plane through π-π stacking for hydrophobic molecules and hydrogen bonding for hydrophilic molecules.

The strong affinity of GO towards all chemical and biological molecules and sieving properties of the porous GO layers can provide a beneficial surface for adhesion of targeted molecules for non-labeled sensing mechanism. By varying the number of GO layers comprising each of the panels 22, the sensor structure 20 can be tuned for control over sieving and molecular adsorption as well as extending the sensitivity of the sensor structure 20 due to enhanced adhesion of targeted molecules. In some embodiments, one or more polymers can be deposited onto one or more of the GO-based panels 22 to render the panel 22 (and thus the structure 20) biocompatible, for example as a small-sized subcutaneously implantable scanner for in vivo measurement of biological species.

As a point of reference, the strong affinity towards all molecules and sieving properties of GO may have been explored for the development of electrochemical, optical and mass sensors for the detection of biological and gas molecules, and humidity sensing. However, the most common sensing technique involves the use of fluorescence quenching by GO, thereby severely limiting potential viability due to the labor-intensive methods and the availability of dyes for the detection process. Furthermore, other non-labeled GO-based detection strategies involve the use of Raman spectroscopy. However, in order to enhance the Raman signal, surface modification techniques are required that involve complex fabrication procedures and lack reproducibility. The optional GO-layer panels 22 of the sensor structures 20 of the present disclosure overcome these concerns.

Regardless of a material utilized for the panels 22, connection of neighboring panels 22 at the corresponding structure corner 26 can be provided in a variety of fashions. In some embodiments, the neighboring panels 22 are in direct, physical contact at the corresponding structure corner 26. In other embodiments, a joint body can be provide at one or more or all of the structure corners 26. The joint body can be formed of a material differing from a material of the panels 22, selected to maintain the 3D shape of the structure 20 and to not interfere with use of the structure 20 as a resonator-type sensor (e.g., the joint body is a non-metallic material that is transparent to THz waves). For example, the joint body can be a polymer. As described in greater detail below, in some embodiments a material of the joint body is selected to facilitate manufacture or assembly of the 3D structure 20.

The resonator or resonator pattern 24 provided with each panels 22 is formed of a metallic, electrically conductive material (e.g., gold) and can comprise resonator segments 30, 32. The resonator pattern 24 can be identically formed on each of the panels 22. The resonator segments 30, 32 can be identical, and can render the resonator pattern 24 to have a symmetrical shape. In some embodiments, the resonator pattern 24 is an "X" shape, with the resonator segments 30, 32 extending between opposing corners of the corresponding panel 22. For example, the panels 22 can each have four panel edges, with first, second, third and fourth edges 40a, 42a, 44a, 46a labeled for the first panel 22a in FIG. 1A. The resonator pattern 24a provided with the first panel 22a includes the first resonator segment 30a extending between a panel corner formed by the first and fourth panel edges 40a, 46a and a panel corner formed by the second and third panel edges 42a, 44a. The second resonator segment 32a extends between a panel corner formed by the first and second panel edges 40a, 42a and a panel corner formed the third and fourth panel edges 44a, 46a. The resonator pattern 24a terminates slightly away from (and does not contact or encompass) the panel edges 40a-46a. For example, and as more clearly shown in the enlarged view of FIG. 1B, the first resonator segment 30a terminates at an end defined by first and second resonator edges 50a, 52a. The first resonator edge 50a is the surface of the first resonator segment 30a most-proximate the second panel edge 42a, and is slightly spaced from the second panel edge 42a; the second resonator edge 52a is the surface of the first resonator segment 30a most-proximate the third panel edge 44a, and is slightly spaced from the third panel edge 44a.

In some embodiments, a major plane of the first resonator edge 50a is substantially parallel (i.e., within 5 degrees of a truly parallel relationship) with the second panel edge 42a, and a major plane of the second resonator edge 52a is substantially parallel with the third panel edge 44a. The resonator segments 30, 32 carried by the remaining panels 22 can have a similar geometry and relationship relative to edges of the corresponding panel 22, as shown, for example, by the resonator segment 32b carried by the second panel 22b and resonator segment 32c carried by the third panel 22c in FIG. 1B. With this construction, the resonator segments 30, 32 (FIG. 1A) of neighbor panels 22 are aligned with, and spaced from, one another. For example, the first resonator edge 50b of the second panel resonator segment 32b is aligned with, but spaced from, the first resonator edge 50a of the first panel resonator segment 30a. Stated otherwise, the first and second panels 22a, 22b effectively intersect at the structure corner 26a. The first panel resonator edge 50a and the second panel resonator edge 50b are aligned with, and electromagnetically coupled to, one another relative to the structure corner 26a, and are spaced from one another by a gap or a split g (i.e., a three-dimensional gap). A similar relationship is established between the second resonator edge 52a of the first panel resonator segment 30a and the first resonator edge 50c of the third panel resonator segment 32c relative to the corner structure 26b defined between the first and third panels 22a, 22c; and between the second panel resonator edge 52b and the third panel resonator edge 52c relative to the corner structure 26c defined between the second and third panels 22b, 22c. In some non-limiting embodiments, a distance between the resonator edge and the corresponding panel edge (e.g., distance between the first resonator edge 50a and the second panel edge 42a) can be on the order of 0.5-5.0 μm, and a size of the 3D gap g separating electromagnetically coupled resonator segments of neighboring panels (e.g., a distance between the first panel resonator edge 50a and the second panel resonator edge 50b) can be on the order of 15-40 μm, and in other embodiments in the range of 21-35 m; other dimensions are also acceptable. As point of reference, the size of the 3D gap g can be greater than twice the 2D distance or gap between resonator edge and corresponding panel due to presence of a hinge or joint that interconnects the neighboring panels, a thickness of the neighboring panels, etc.

Figure 1B:
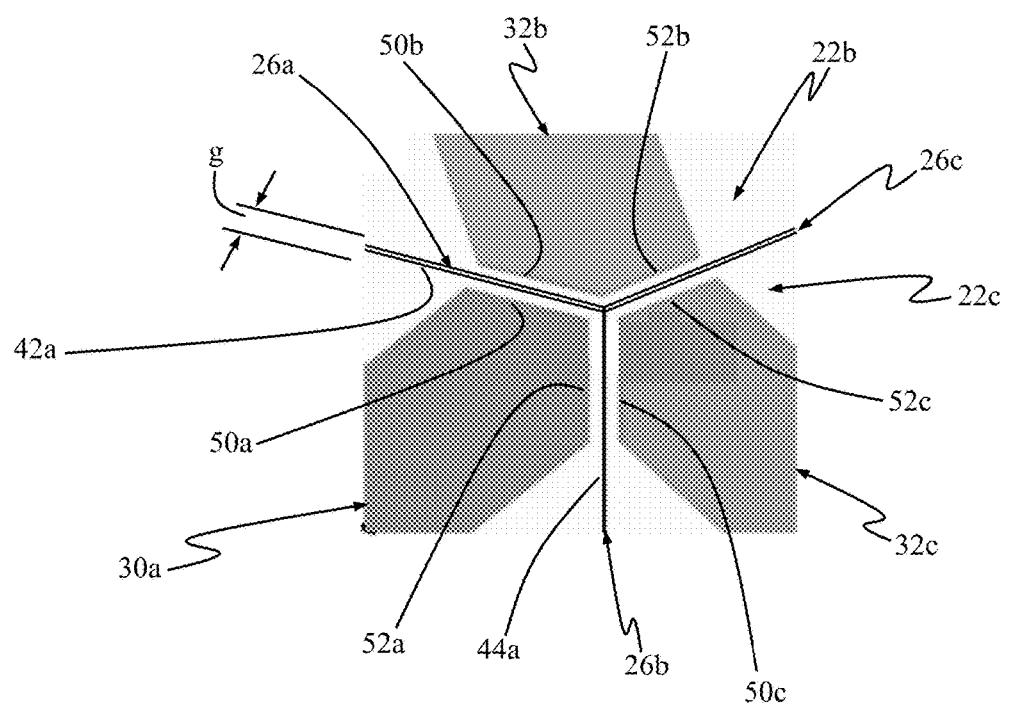
FIG. 1B is an enlarged view of a portion of the metamaterial structure of FIG. 1A as designated by the line 1B in FIG. 1A.

With the non-limiting embodiment of the 3D octagram split-ring resonator (OSRR) of FIGS. 1A and 1B, the eight (8)-pointed 3D octagram ensures uniform coupling to each split-ring resonator (SRR) in all directions for any orientation, thus overcoming the anisotropic polarization dependent transmission response of the two-dimensional (2D) C-shaped SRR structure. As further discussed below, the sensitivity of the 3D OSRR in comparison to the 2D coupled net is presented where the 3D uniform coupling between the metallic resonant segments enhances the sensitivity of the SRR structures. Due to the isotropic behavior and high sensitivity, the innovative three dimensionally coupled OSRR can be used for fast, non-contact, non-labeled detection of chemical and/or biomolecules without the ambiguity produced by the anisotropy of the structure.

Figure 2A:
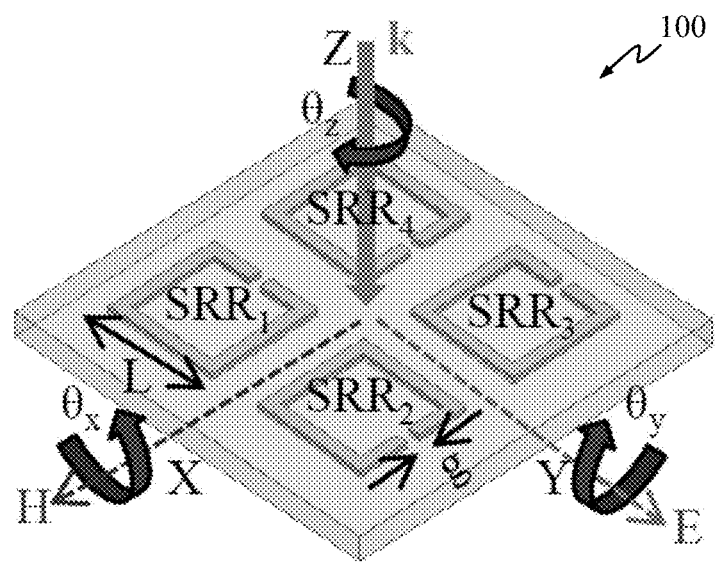
FIG. 2A schematically illustrates a 2D unit cell including an array of four C-shaped split-ring resonators.

By way of further background explanation, FIG. 2A schematically depicts a unit cell 100 of four, identically sized and shaped split-ring resonators $SRR_1$-$SRR_4$, each forming a gap or split g. The split-ring resonators $SRR_1$-$SRR_4$ are oriented such that the first and third split-ring resonators $SRR_1$, $SRR_3$ have a magnetic field H perpendicular to the gap g ($1^{st}$ mode), while the second and fourth split-ring resonators $SRR_2$, $SRR_4$ have electric field E perpendicular to the gap g ($2^{nd}$ mode). Using ANSYS Electromagnetics version 16.0.0 available from ANSYS, Inc. of Canonsburg, Pa., the structure for the unit cell 100 where each of the four split-ring resonators $SRR_1$-$SRR_4$ has a length (L)=36 μm, and split gap (g)=4 μm was simulated (further details on the simulations are provided in the Examples section below). In such a configuration, on rotations of the unit cell 100, the decrease in $1^{st}$ mode resonance of the first split-ring resonator $SRR_1$ is compensated by a proportional increase of $1^{st}$ mode resonance for the second split-ring resonator $SRR_2$, and vice-versa for $2^{nd}$ mode as well. The third and fourth split-ring resonators $SRR_3$, $SRR_4$ ensure that the resonators within the unit cell 100 couple equally in all directions. However, when angles between the incident wave and SRR surface are changed in X-axis, Y-axis, and Z-axis (when 3D rotations of the unit cell 100 are applied), the $1^{st}$ mode resonance shows a large change in the resonance frequency, as well as the transmission amplitude. Thus, the 2D SRR structures, even with varying unit cell, cannot provide a three dimensionally isotropic transmission response (where an isotropic transmission response represents that rotation about any axes would not change the amplitude and/or resonance frequency).

Figure 2B:
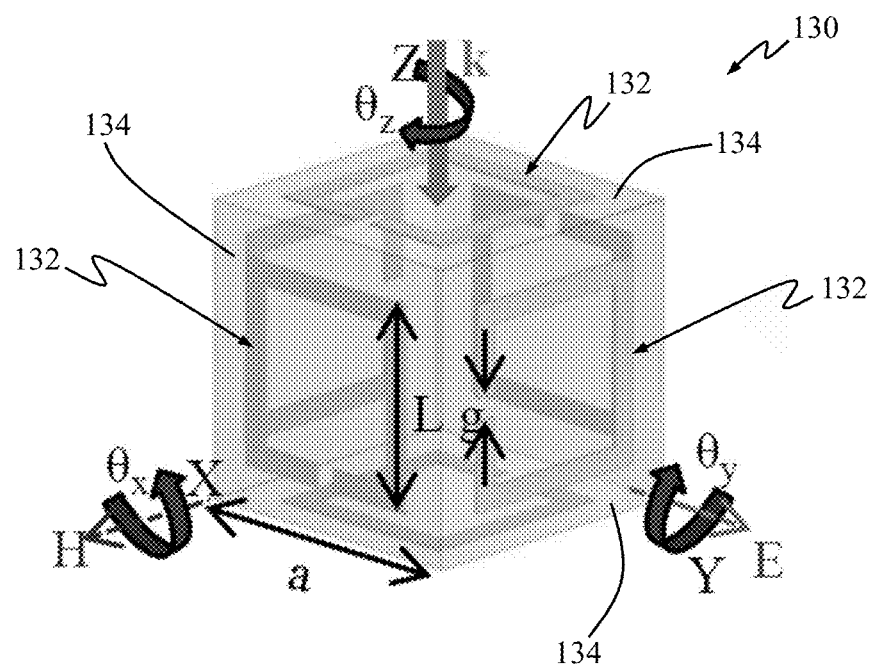
FIG. 2B schematically illustrates a 3D cubic structure with a C-shaped split-ring resonator on each face of the cubic structure.

One possible technique for partially addressing the anisotropic concerns is shown in FIG. 2B and includes a cubic structure 130 with 2D split-ring resonators 132 patterned on respective faces 134 of the cubic structure 130. However, using this approach, the split-ring resonators 132 and the corresponding split g continues to remain two dimensional; this induces non-uniform coupling between the split-ring resonators 132 on different faces 134, resulting in multiple resonance behavior. The resonant arms containing the split g couple strongly to the neighbors owing to the electric field confined with the split g. For the cubic structure 130 shown in FIG. 2B, simulations reveal that at the initial position and for rotations about the Y-axis ($\theta_y$), the orientation of the split g within the split-ring resonators 132 with respect to the polarization direction of the electric field E and the magnetic field H remains the same. However, at $\theta_y$=450, the structure 130 shows a shift in $1^{st}$ mode resonance frequency as well as the transmission amplitude. This shift can be attributed to the non-uniform coupling of each of the split-ring resonators 132 to its neighboring resonators 132 (a split-ring resonator with an electric field E perpendicular to the plane), resulting in an anisotropic resonance behavior.

Figure 2C:
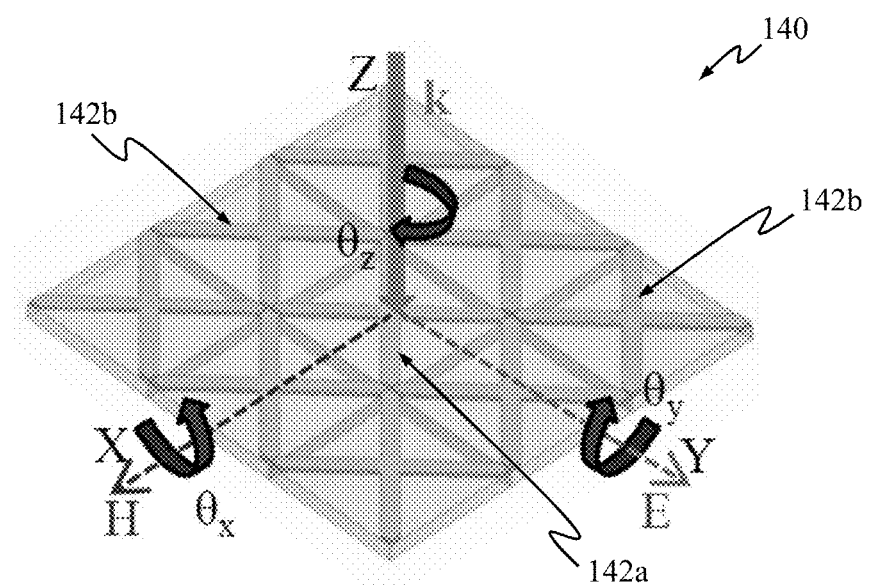
FIG. 2C schematically illustrates a 2D unit cell including an array of nine split-ring resonators.
Figure 2D:
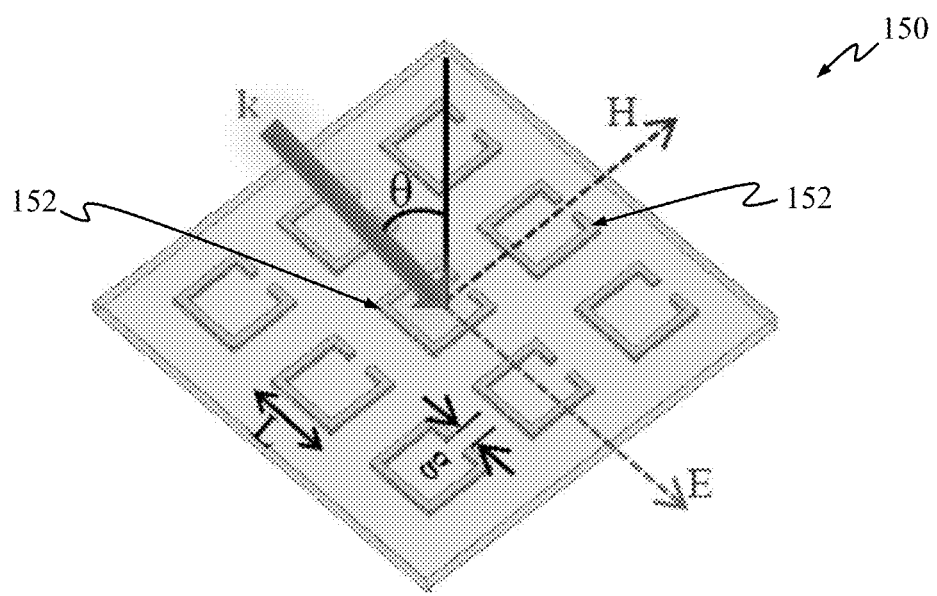
FIG. 2D schematically illustrates a 2D unit cell including an array of nine C-shaped split-ring resonators.

The above anisotropy in the transmission response implicates the need for symmetric resonators that minimize the non-uniform coupling to their neighbors. FIG. 2C depicts another structure 140 with a fully symmetric two dimensional array of split-ring resonators, including a center resonator 142a and edge resonators 142b. The non-uniform coupling reduces the isotropy of the structure 140, giving it overlapping multiple resonant peaks. For FIG. 2C, the resonator 142a at the center of the unit cell structure 140 couples equally in all directions in the XY plane. However, the edge resonators 142b surrounding the center resonator 142a can only couple to half as many resonators since the edge resonators 142b at the edges of the unit cell structure 140 have lesser neighbors than the center resonator 142a. This produces multiple transmission drops that correspond to the resonance of each resonator 142a, 142b within the unit cell 140. The first drop corresponds to the resonance of the center resonator 142a as seen by strong surface current for the center resonator 142a (lowest resonance frequency due to highest coupling). The peaks at higher frequency correspond to the edge resonators 142b, giving them a higher surface current at a higher frequency. When the 2D non-uniformly coupled unit cell 140 is rotated, the transmission response is rendered incomprehensible due to the multiple resonances. Similar results are obtained for a 2D unit cell 150 including an array of nine partially symmetric C-shaped split-ring resonators 152 shown in FIG. 2D.

The non-uniform 2D coupling presents a major hurdle in achieving an isotropic 3D transmission response, a response that can, for example, be beneficial for the application of a split-ring resonator-based sensor for in vivo detection where rotation angles of the sensor cannot be accessed or controlled. Returning to FIGS. 1A and 1B, the 3D microscale metamaterial structures 20 of the present disclosure overcome the multiple peaks caused by non-uniform coupling, and the anisotropy due to the switching between $1^{st}$ and $2^{nd}$ mode described above. In some embodiments, the structures 20 of the present disclosure are configured such that each resonator 24 couples to an equal number of neighboring resonators 24, and at each angle of rotation of the structure 20 an equal number of the resonators 24 demonstrate $1^{st}$ and $2^{nd}$ mode. In some embodiments, the 3D microscale structure 20 can be considered to be a 2D unit cell folded into a 3D cube consisting of six (6) faces (i.e., six of the panels 22) with one of the resonators 24 on the face of each of the panels 22, such that the resonator segments 30, 32 of each of the resonators 24 are forced to couple to their neighbor through the split g created at the corners of the structure 20 thus forming a fully symmetric eight (8) pointed 3D star. Considering the resonator 24b at the top face of the cube structure 20 in FIG. 1A, the split g (FIG. 1B) at the corner of the X-shaped segments couple it equally in all directions to the resonators 24 on the side walls of the cube structure 20 which in turn couple to the resonator 24 at the bottom face. The split at the corner and the strong uniform coupling between the segments 30, 32 on each face of a cube effectively creates a 3D octagram based split-ring resonator (OSRR). Since the split is three-dimensional, it is equally affected by the E, H and k vectors for all orientations of the cube.

Figure 3:
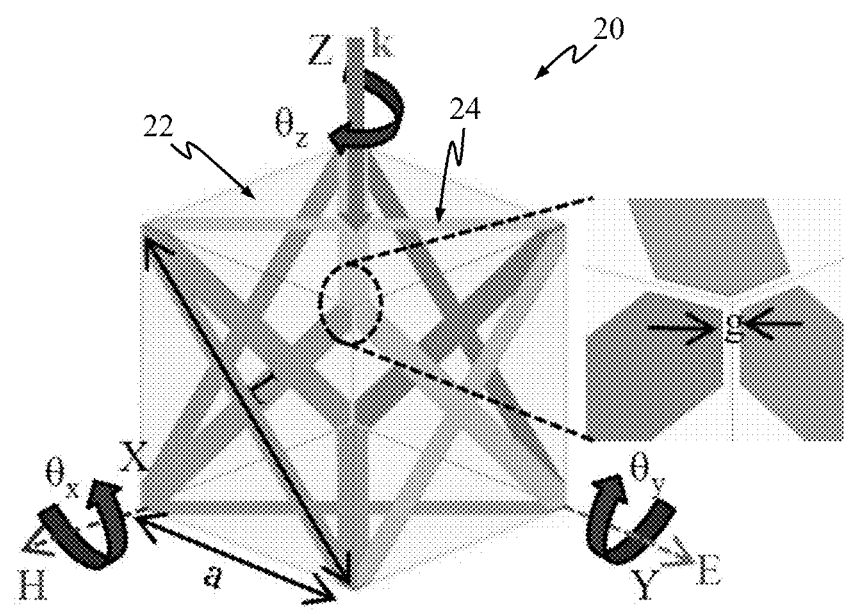
FIG. 3 schematically illustrates the metamaterial structure of FIGS. 1A and 1B with various parameters identified.

By way of non-limiting example and with reference to FIG. 3, the cubic structure 20 was simulated using ANSYS Electromagnetics version 16.0.0, using an epoxy (available from MicroChem Corp. or Newton, Mass. under the trade designation SU-8) for the panels 22, gold for the resonator patterns 24, a cube length (a) of 500 µm, a resonator length (L) of 674 µm, and a gap or split (g) of 16.55 µm. Additional details on the simulation parameters are provided in the Examples section below. The simulations at different rotations of the structure 20 are reported in FIG. 4, and show an isotropic transmission response with a single resonant drop at 0.13 THz, and with the same transmission amplitude which is invariant under 3D rotations. The 3D nature of the metamaterial structure 20 is further evidenced by the strong surface current at all the faces of the structure 20 as reflected by the representation of current distribution at 0.13 THz of FIG. 5. In the absence of the 3D coupling, when the electric field E is polarized perpendicular to the surface of any one of the resonator 24, no resonance is observed and the surface current is zero (0). However, the 3D coupled system acts as a single resonant structure, for the 3D OSRR 20 each resonant segment 30, 32 induces resonance in its neighbor, creating a uniform surface current on all 3D surfaces.

Figure 6:
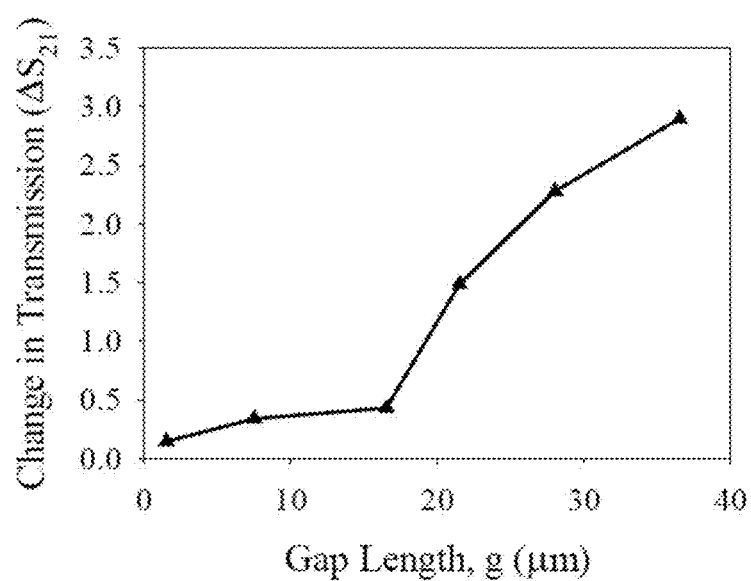
FIG. 6 is a graph of change in simulated transmission responses for the metamaterial structure of FIG. 3 at different gap sizes.
Figure 7:
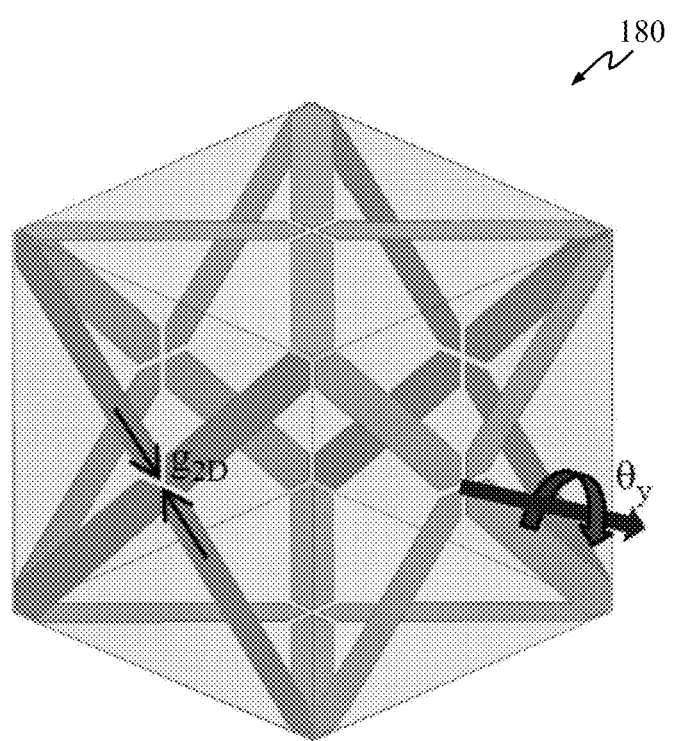
FIG. 7 schematically illustrates another metamaterial structure of the present disclosure.

When the 3D split gap g between the resonant segment pairs 30, 32 (FIG. 1A) of neighboring panels 22 changes, the coupling between them also varies. By way of non-limiting example, FIG. 6 provides the results of simulations using the parameters described above at different gap g sizes. When the gap g is small (1.5-16 µm), the structure 20 acts as a single 3D resonator due to the strong coupling between the resonators 24 defined on each panel of the cube structure 20, and the response is isotropic with well-defined resonance drops. However, as the gap increases (g=21 µm), the coupling between resonant pairs decreases, causing them to act as six independent resonators giving a more anisotropic response with larger changes in transmission amplitude at resonance between different orientations. Addition of a 2D gap $g_{2D}$ to the individual resonators 24 of the 3D OSRR 20 may also affect the isotropy of the structure 20. When a 2D gap of length $g_{2D}$ in the middle of the resonators is added to a 3D OSRR structure 180 as in FIG. 7, the isotropic response of the symmetric OSRR reverts to that of the non-uniformly coupled 2D resonators, resulting in an anisotropic resonance behavior.

Figure 8A:
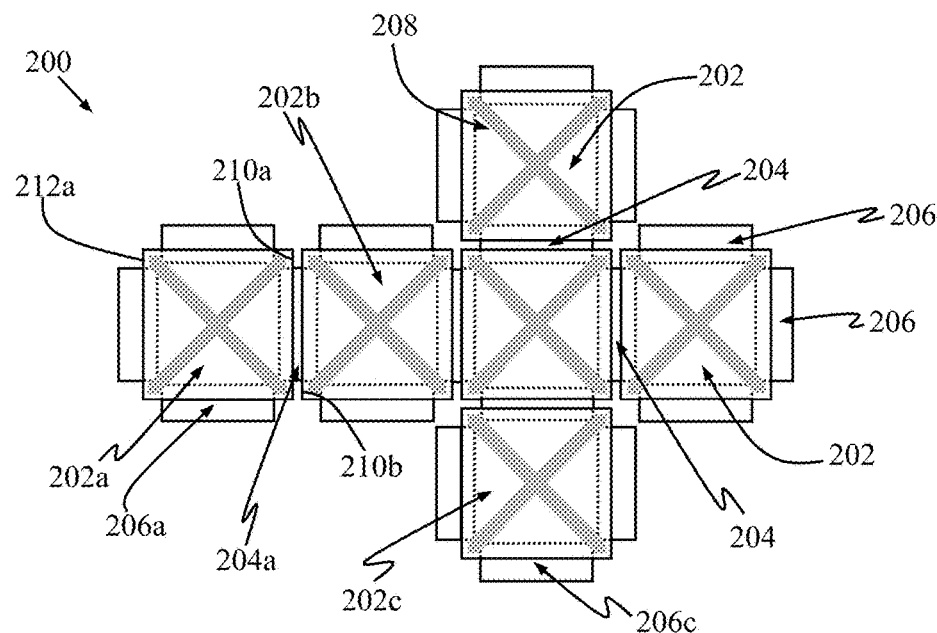
FIG. 8A is a simplified top plan view of a 2D net useful in forming a 3D microscale metamaterial structure in accordance with principles of the present disclosure.

Some aspects of the present disclosure relate to the fabrication of the 3D microscale metamaterial structures described above using a self-folding manufacturing technique. In general terms, the self-folding process is akin to origami in which a 2D microscale structure or net self-folds into a 3D microscale structure. For example, FIG. 8A illustrates a 2D net 200 from which a 3D microscale structure of the present disclosure can be generated. The 2D net includes a plurality of microscale panels 202, hinges 204 and optional joint structures 206. Each of the panels 202 can be a continuous or homogenous body. In other embodiments, each of the panels 202 can include an outer frame forming a window in which a membrane is disposed (and is supported by the outer frame) as described, for example, in U.S. Patent Application Publication Nos. 2017/0294698 and 2017/0291819, the entire teachings of each of which is incorporated herein by reference. Regardless, a resonator or resonator pattern 208 is formed on or carried by each of the panels 202. The panels 202 and the resonators 208 can have any of the forms described above (e.g., the panels 202 are a polymer, GO layers, etc.; the resonators 208 are formed of an electrically conductive metal, and have the geometry and spatial relationships relative to edges of the corresponding panel 202 as described above). Respective ones of the hinges 24 extend between and interconnect opposing edges of immediately adjacent ones of the panels 22 in the array of the 2D net 20. A material of each of the hinges 24 is selected to exhibit desired properties when subjected to an environmental changes, such as in the presence of heat, and in some embodiments is a polymer (e.g., photoresist), solder (Pb—Sn), etc.

As initially provided in the form of the 2D net 200, the panels 202 are arranged in an array conducive to folding into a 3D polyhedral shape, with facing edges of immediately adjacent ones of the panels 202 being connected to one another by a corresponding one of the hinges 204. Stated otherwise, in the 2D net array, various panels 202 are arranged side-by-side or edge-to-edge; one of the hinges 204 extends between and interconnects the corresponding edges thereof. For example, first and second panels 202a, 202b are identified in FIG. 8A. In the array, the first panel 202a is immediately adjacent the second panel 202b, with a first edge 210a (referenced generally) of the first panel 202a facing or immediately proximate a first edge 210b of the second panel 202b. The first and second panels 202a, 202b are interconnected by a hinge 204a that extends between the first edges 210a, 210b. Other panel edges in the array of the 2D net 200 are free or not otherwise directly connected to another panel by a hinge. For example, a second edge 212a of the first panel 202a identified in FIG. 8A is not directly connected to a separate panel in the 2D net 200 state. In some embodiments, a joint structure 206 is provided at one or more (including all) of the panel free edges. Where provided, the joint structure 206 projects beyond the face of the corresponding panel 202 (e.g., FIG. 8A identifies joint structure 206a that is applied to the first panel 202a at the second edge 212a). A material of each of the joint structures 206 can be identical to that of the hinges 204 (e.g., polymer) for reasons made clear below.

Figure 8B:
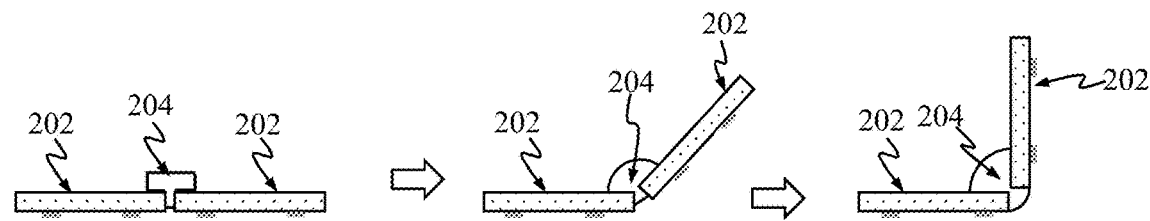
FIG. 8B schematically illustrates portions of methods of the present disclosure.
Figure 8C:
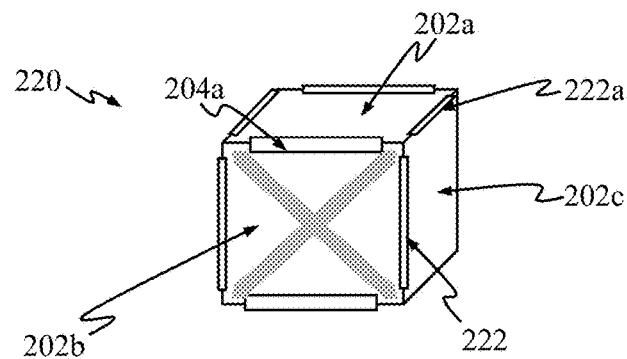
FIG. 8C is a simplified perspective view of a 3D microscale metamaterial structure resulting from the 2D net of FIG. 8A.

In some embodiments, the 2D net 200 is configured such that when the 2D net 200 is subjected to energy (e.g., heat), a temperature of the hinges 204 is raised to a critical point (e.g., melting point); the molten hinges 204 generate a surface tension force and cause the panels 202 to self-fold up into a 3D micro-scale structure (e.g., as a result of the polymer hinge melting (or reflow), a surface tension force is generated). For example, FIG. 8B schematically depicts self-folding of the hinge 204 and two of the panels 202 when the hinge 204 is subjected to heat. FIG. 8C illustrates a 3D microscale metamaterial structure 220 resulting from origami-like self-folding of the 2D net 200. As a point of reference, and with additional reference to FIG. 8A, where provided, various ones of the joint structures 206 are brought into contact with one another and fuse upon self-folding of the 2D net 200, resulting in a completed joint 222 at a corresponding edge of the 3D microscale metamaterial structure 220. For example, the first joint structure 206a is identified with the first panel 202a in FIG. 8A, as is a first joint structure 206c provided with a third panel 202c. The first-third panels 202a-202c are again labeled in FIG. 8C, along with the hinge 204a. With cross-reference between FIGS. 8A and 8C, one completed joint 222a of the 3D microscale metamaterial structure 220 is generated by the first joint structure 206a of the first panel 202a and the first joint structure 206c of the third panel 202c upon completion of the self-folding operation.

The 2D net and resultant 3D microscale metamaterial structures of the present disclosure can assume a wide variety of other shapes, such as any polyhedral shape, and are not limited to the cubic shape of FIG. 8C.

Embodiments and advantages of features of the present disclosure are further illustrated by the following non-limiting examples, but the particular materials and amounts thereof recited in these examples, as well as other conditions and details, should not be construed to unduly limit the scope of the present disclosure.

EXAMPLES

Figure 9A:
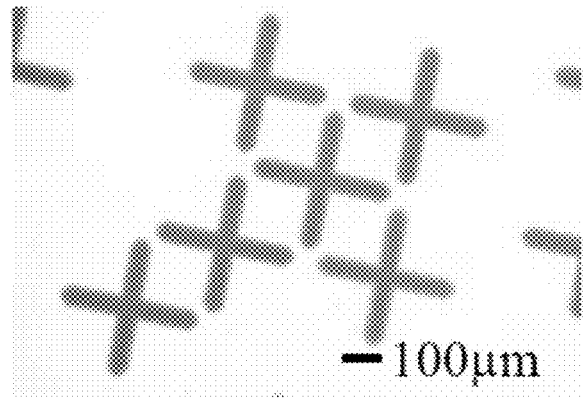
FIGS. 9A-9D are optical images of construction of a sample 3D microscale metamaterial structure described in the Examples section.
Figure 9B:
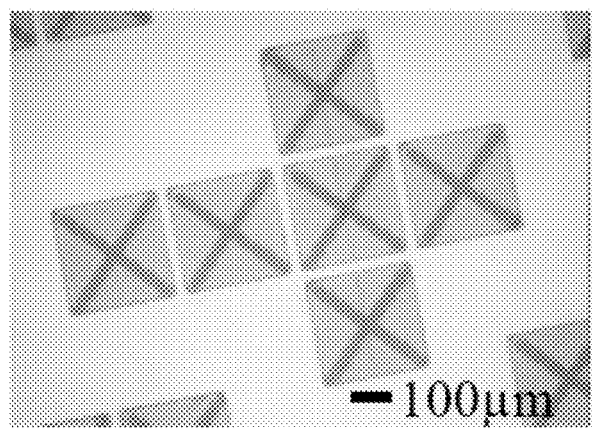

Provided as one illustrative example, 3D microscale metamaterial structures in accordance with principles of the present disclosure, and in particular 3D OSRR as isotropic octagrams, were fabricated as 500 m sized cubes with symmetric resonator segments using a self-assembly process. A 10 nm chromium (Cr) layer was deposited onto a silicon wafer using electron beam (E-beam) evaporation. A 100 nm copper (Cu) layer was deposited onto the Cr layer using E-beam evaporation. The Cr—Cu layers combined to serve as a sacrificial later as described below. Split-ring resonator patterns (akin to the patterns of FIG. 8A) were formed on the Cu layer by first depositing a Microposit® S1813 photoresist (MicroChem Corp., Newton, Mass.) that was then spun at 2000 rpm (for a thickness of 1.8 µm), followed by a soft-bake at 115° C. for 1 minute. The photo resist was patterned using a photolithography process with a glass-mounted mask though a UV-exposed in a mask aligner, and was then developed in a developer solution Microposit® MF®-319 (MicroChem Corp., Newton, Mass.) for 90 seconds with agitation. 300 nm thick gold (Au) was formed in the pattern of the photoresist by electroplating a gold plating formulation Techni Gold® 25 ES (Technic Inc., Cranston, R.I.) for 20 minutes. The photoresist (S1813) was then removed using acetone. FIG. 9A is an image of the resultant gold resonator patterns on the Cu layer. Panels were then formed over the gold resonator patterns by spin coating a photodefinable epoxy SU-8™ (from MicroChem Corp., Newton, Mass.) at 4000 rpm (for a thickness of 10 µm), followed by soft-baking at 95° C. for 2.5 minutes. The sample was then UV-exposed in a mask aligner followed by a post-bake at 95° C. for 3.5 minutes. The SU-8 epoxy was then developed in a developer SU-8™ developer (from MicroChem Corp., Newton, Mass.) for 2.5 minutes, and then hard-baked at 200° C. for 15 minutes to further cure the photoresist. FIG. 9B is an image of the resultant sample.

Figure 9C:
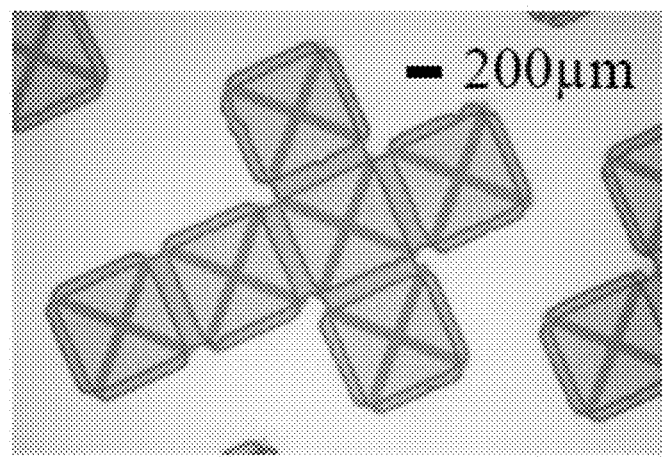

Hinges (akin to the hinges 204 of FIG. 8A) were then formed on the sample by first spin coating a positive photoresist Megaposit™ SPR™ 220-7.0 (from MicroChem Corp., Newton, Mass.) two times at 1000 rpm to yield a thickness of 21 m for the hinges. The sample was left undisturbed for 3 minutes to even out the photoresist, followed by three baking steps of 60° C. for 30 seconds, 115° C. for 90 seconds, and 60° C. for 30 seconds. Following the baking steps, the sample was left undisturbed for 3 hours, and then UV-exposed in a mask aligner for 120 seconds and developed in AZ® Developer (from Micro-Chemicals GmbH) for 120 seconds. FIG. 9C is an image of the resultant sample (i.e., 2D net with six panels interconnected by hinges). The sample was then submerged in a Cu etchant (APS-100™ Copper Etchant from Transene Company, Inc.) to etch the Cu sacrificial layer and release the 2D net structure from the silicon wafer.

Figure 9D:
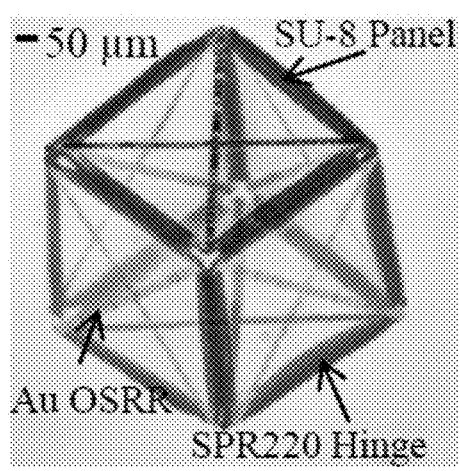

The released 2D net structure was transferred from the Cu etchant to a container of deionized water using droppers. The container was placed on a hot plate and the temperature was gradually increased from 100° C. to 250° C. until the water boiled. The hinges reflowed under the higher temperatures and generated a surface tension force between the panels, causing the 2D net structure to self-fold into a 3D cubic structure. Upon cooling, the hinges re-solidified and secured the shape of the 3D cubic structure. FIG. 9D is an image of the resultant 3D sample structure. The SPR 220 hinges and the SU-8 panels ensure that the Au SRRs were the only metallic resonant structures present, and the remainder of the polymer based cube is transparent to the THz waves. The cubic structure had a length of 500 µm, and a gold SRR on each face of the cube. The gold had a thickness of 300 nm. The gap between resonator segments of neighboring panels (i.e., the gap g in FIG. 1B) was 35 µm.

The sample cubic structure fabricated by the above-referenced self-folding process was characterized using terahertz (THz) time-domain spectroscopy (0.1 THz to 1.0 THz). For measurement, the sample cubic structure was attached to a piece of double sided transparent tape (e.g., Scotch brand tape available from 3M Company of Maplewood, Minn.), which is transparent to the incident THz light. The tape with the sample cubic structure was fixed onto a 3 mm diameter aperture or a 1 mm diameter aperture. The aperture was attached to a rotational mount and rotations were only performed about the Z-axis ($\theta_z$ in FIG. 3) due to lack of a tri-axes rotational mount. A THz pulse generated from a commercial GaAs emitter (Tera-SED planar large-area GaAs based photo-conductive emitter from Laser Quantum Ltd., Cheshire, UK) passed through the aperture with the sample cube and was received by the detector. The GaAs emitter was illuminated by a 130-fs Ti:sapphire laser pulse train with 780 nm center wavelength and 80 MHz repetition rate (MaiTai® XF Ti:sapphire oscillator from Spectra-Physics, Santa Clara, Calif. (a Newport Company)). The P-polarized THz pluses were normally incident on the surface of the 3D sample structure, and the sample structure was rotated from 0°-360° along the propagation axis of the incident wave to verify its polarization-independent property. The transmission spectra of both the sample structure (i.e., sample 3D OSRR) and a reference cube without the metallic patterns was measured using the electro-optic sampling method with a (110)-oriented ZnTe crystal. After taking the Fourier transform of the transmitted time-domain signal, the amplitude of transmission spectra on the frequency domain was normalized by the reference signal. Minor differences in the position of the reference cube and the sample cubic structure cased the transmission response to be less than 1.0 at a few frequencies. A 10% error may be expected due to the mismatch in position between the reference cube and the sample cubic structure resulting from the manual placement of the cube to be tested on the aperture.

Figure 4:
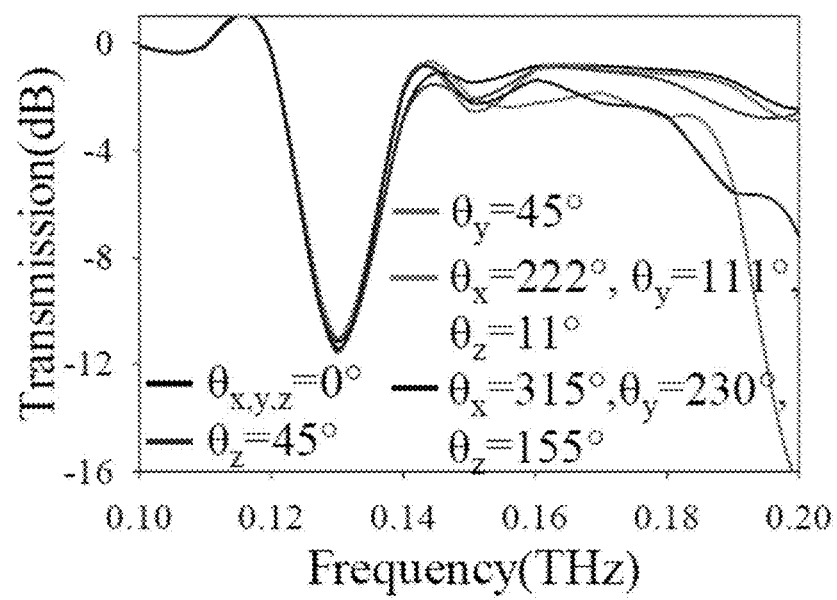
FIG. 4 is a graph of simulated transmission responses for the metamaterial structure of FIG. 3 at different rotational orientations.
Figure 5:
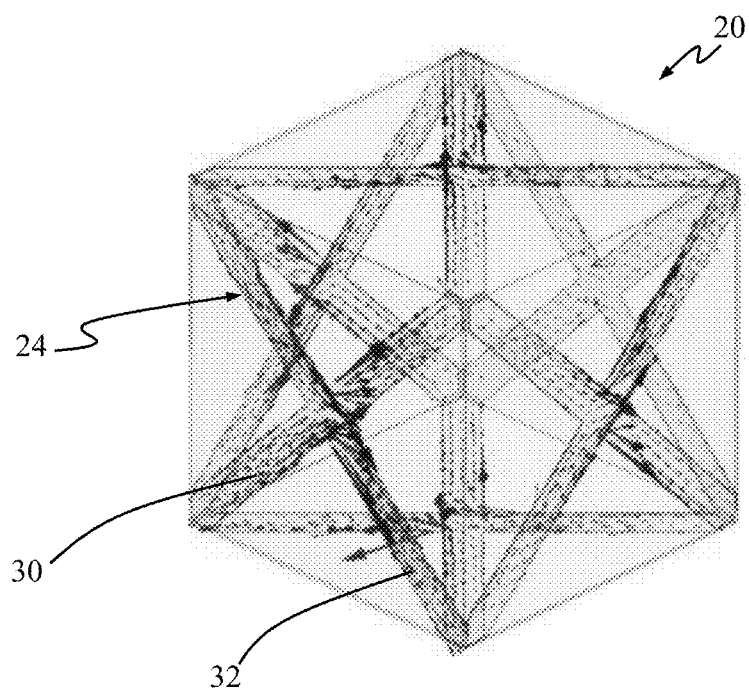
FIG. 5 schematically illustrates simulated current distribution of the metamaterial structure of FIG. 3.
Figure 10A:
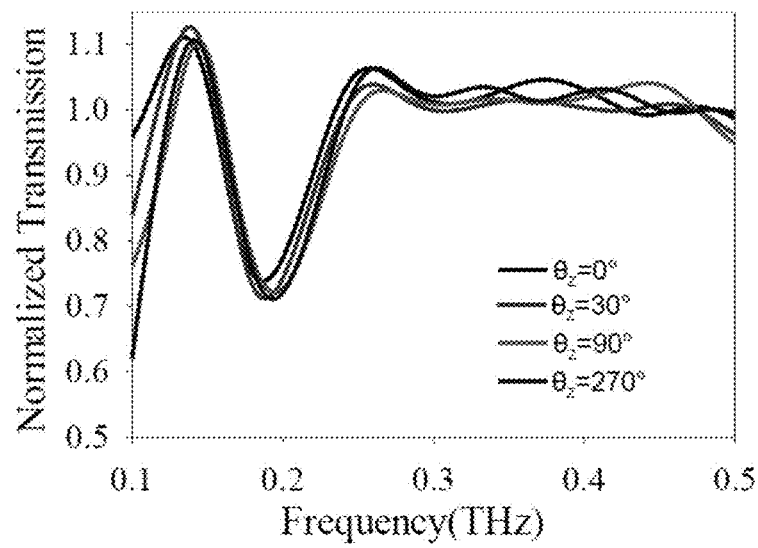
FIG. 10A are plots of measured transmission data at a 3 mm test aperture as described in the Examples section.
Figure 10B:
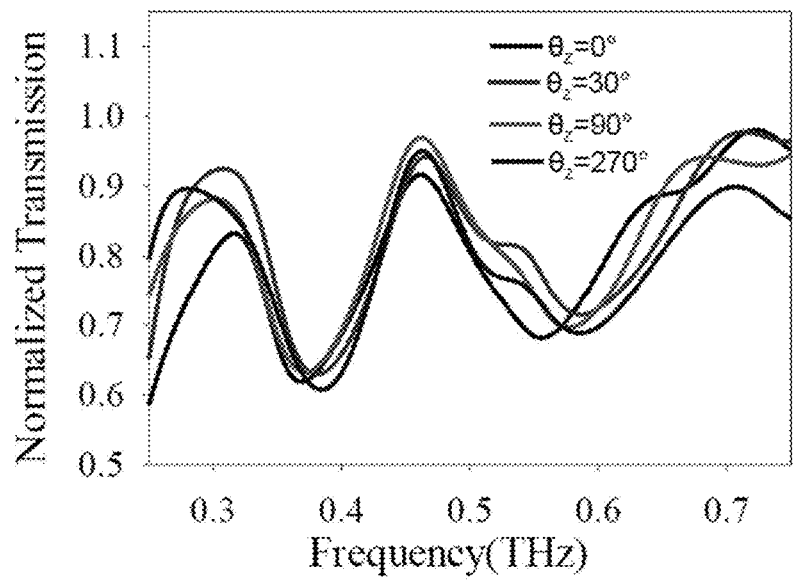
FIG. 10B are plots of measured transmission data at a 1 mm test aperture as described in the Examples section.

The results of the measurements for the 3 mm aperture are reported in FIG. 10A; the results of the measurements for the 1 mm aperture are reported in FIG. 10B. The cut-off frequency for the 3 mm aperture was found to be ~0.3 THz; for the 1 mm aperture, the cut-off frequency was ~0.1 THz. The $1^{st}$ mode resonance could be measured using the 3 mm aperture and was found to be 0.18 THz (FIG. 10A). The results of the measurement are almost equal to the simulated resonance frequency described above of 0.13 THz (FIG. 4). The $1^{st}$ mode resonance frequency and amplitude using the 3 mm aperture was measured to be constant for the various values of $\theta_z$ similar to the simulated transmission response (FIG. 4) with a single peak that remains invariant in amplitude and frequency for different orientation of the cube demonstrating the isotropic transmission response of the 3D OSRR due to the uniform coupling between the resonators and the 3D gap. However, the higher order modes could not be observed with an aperture diameter of 3 mm since only 33% of the area of aperture was covered by cube, generating a large amount of noise to view the weaker higher order modes.

The 1 mm aperture was used to view the higher order mode for the cubic sample, with the same steps used for rotation as described above. As shown in FIG. 10B, the $2^{nd}$ mode resonance the frequency was found to be 0.35 THz; when rotated around the Z-axis, the isotropy for the $2^{nd}$ mode was found to be slightly weaker than that for the $1^{st}$ mode measured with the 3 mm aperture (FIG. 10A). A maximum shift of 0.01 THz in resonance frequency, and a maximum difference of 0.05 in transmission was measured between the orientations with least isotropy. This difference could be attributed due to the noise generated from the circular aperture for the measurement of a single 500 m cube which introduces non-uniform boundary spacing which is smaller and closer to the dimensions of the cube for $2^{nd}$ mode measurement.

As mentioned above, various transmission response simulations were performed using Ansys Electromagnetic Suites 16.0.0 (available from ANSYS, Inc. of Canonsburg, Pa.) with a distributive solve over an MPI cluster. The software uses an FEM technique where the 3D structure is divided into tetrahedral elements that are refined over several recursive calculations to produce a fine mesh. Solutions to the Maxwell's equation were found producing an S-matrix where the $S_{21}$ parameter provides the transmission characteristics. The 2D/3D C-shaped Au resonators (FIGS. 2A-2C, C) with the specified length (36 μm), width (4 μm), thickness (300 nm) and gap (4 μm) were simulated on SU-8 substrate/panels. The structure was then encapsulated by a vacuum box, and the excitation ports were applied to the top and bottom of the vacuum box. The SU-8 permanent photoresist was modeled using the commercial parameters provided by MicroChem Corp. of Newton, Mass. with relative permittivity=4.1, dielectric loss tangent=0.015, mass density=1187 kg/m$^3$, and resistivity 2.8×1016 Ωcm. The electrical conductivity of Au was taken to be 4.1×107 S/m.

The 2D unit cell consisting of an array of symmetric resonators (FIG. 2C) was created with 9 X-shaped resonators each of length (L)=674 μm, width=16 μm, and split gap (g)=16 μm. The 3D star shaped OSRR (FIG. 3) on 500 m SU-8 cube were simulated using the material properties described above. The SPR-220 hinge being a polymer acts to slightly shift the resonance frequency but was ignored during the simulation due to computational limitations. The vacuum boxes for the 2D and 3D unit cell were chosen to be large enough, such that distance of the structure from the edge of the vacuum box on rotation did not impact the isotropy of the structures.

A frequency sweep from 0.02-2.0 THz in steps of 0.01 THz was run for a mesh refined over 20 adaptive passes with an error tolerance of 0.02 for the S-parameter. The resulting $S_{21}$ parameter in decibels (dB) was plotted against the frequency to determine the transmission behavior of the structures. The animation of the surface current was used to evaluate the mode of each resonant pair.

Figure 11:
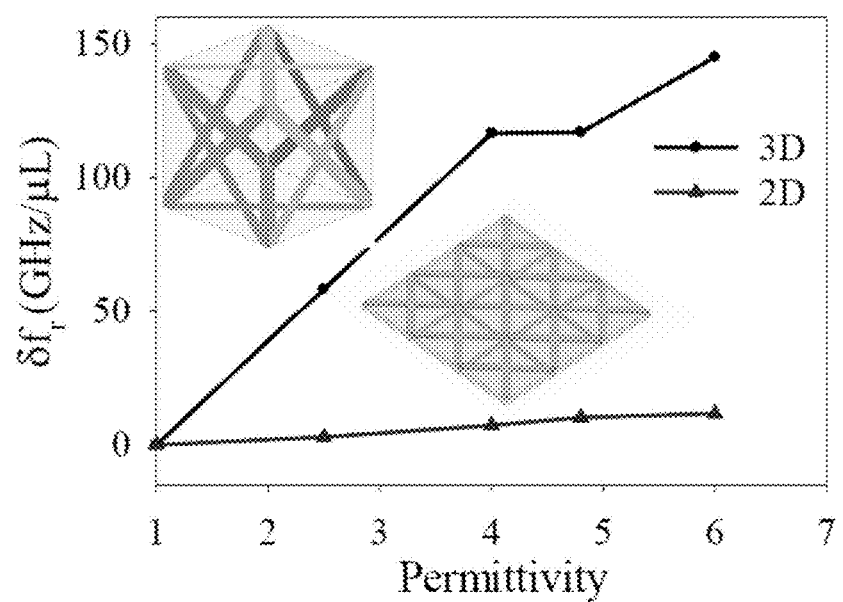
FIG. 11 is a plot of the results of permittivity simulations described in the Examples section.

To demonstrate sensitivity of the sample 3D OSRR, simulations of a 3D octagram (as described above with respect to FIG. 3) and a planar 2D net of symmetric SRRs (as described above with respect to FIG. 2C) were carried out for varying permittivity. The corresponding measurements could not be carried out due to the inability to control the orientation of the small anisotropic 2D resonators on the thin SU-8 panels; hence making it difficult to apply the same conditions to 3D and 2D structures for appropriate comparisons. Moreover, since the aperture size is fixed, the difference in surface area of the aperture covered by the 2D and 3D can lead to discrepancy in the results. When exposed to a biomolecule, the resonant frequency, $f_r = 1/(LC)^{0.5}$ (where L is the inductance due to the gold resonant structure and C is the capacitance of the 2D/3D splits) changes proportional to the relative permittivity ($\epsilon_r$) of the biomolecule being detected. The permittivity was increased from 1 to 6 and the corresponding shift in $1^{st}$ mode resonance per unit volume of the biomolecule was simulated. The results of the simulations are reported in FIG. 11. Unlike a 2D array of SRRs defined on a planar substrate where for small volumes of a target molecule only one of the resonators may demonstrate a change in resonance unable to change the overall response, the metal patterns on each face of the cube are strongly coupled to the neighboring faces. With the cubic metamaterial structures, changes in permittivity surrounding the tips of each resonator cause a domino reaction, providing the isotropic 3D coupled OSRR with a much higher sensitivity than the corresponding 2D coupled SRR. This results in the large shift in resonance frequency which is thirteen times higher for small permittivity changes ($\Delta\epsilon_r=6$) for the 3D OSRR as compared to the 2D planar SRR. Thus, the 3D coupling induces a shift in resonance frequency on exposure to target molecules that is much higher than the corresponding shift for 2D planar sensors, for variations in permittivity from 0 to 6 the 3D OSRR always demonstrated a shift that was at least 10 to 25 times higher than the 2D structure.

Figure 12:
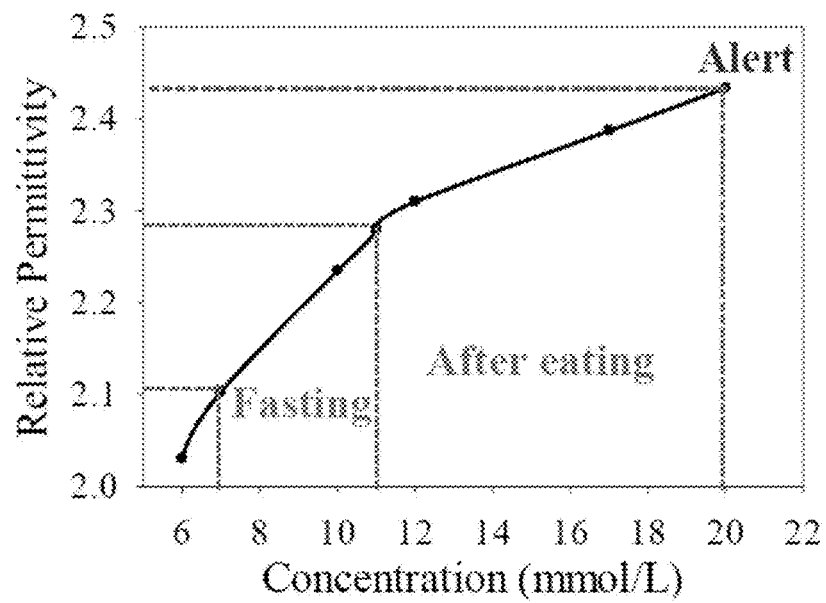
FIG. 12 is a graph of relative permittivity of glucose.
Figure 13:
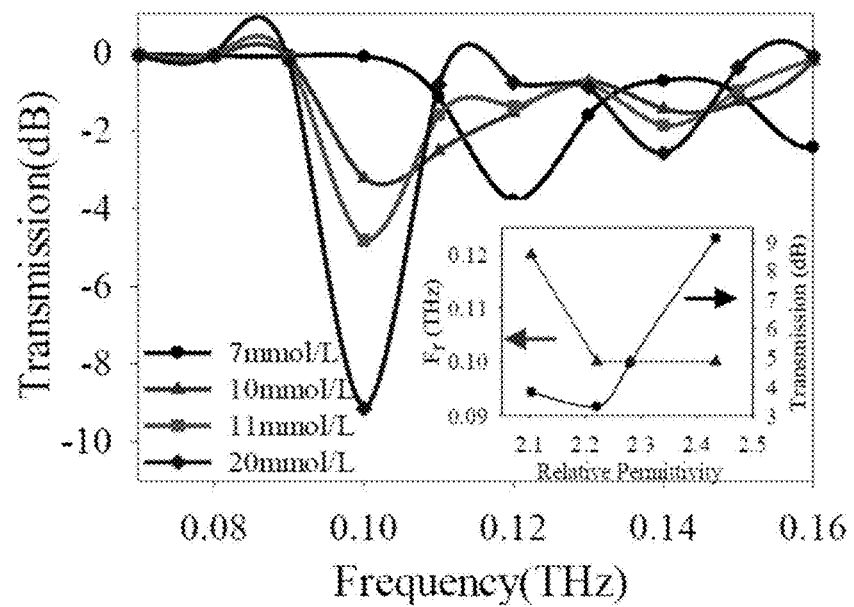
FIG. 13 is a plot of the transmission response of a sample microscale metamaterial structure to different glucose levels as described in the Examples section.

In order to further assess the detection ability of the 3D OSRR structure of the present disclosure for smaller changes in permittivity (as is the case with most biological samples), the simulation of the transmission response was carried out for rising level of glucose level in blood. Glucose was chosen as the targeted substance since the refractive index of blood increases with increase in glucose level and has been studied from GHz-THz range, and the corresponding permittivity can hence be found as the root of refractive index. Three critical levels can be identified for glucose level within the human body. First, the baseline level before eating (fasting), second the level after eating that most humans temporarily undergo, and third the critical level which can result in adverse consequences if not treated immediately. The corresponding change in relative permittivity for the three levels is only 0.35 as shown in FIG. 12. The results of the simulations are reported in FIG. 13. For the fasting condition at a glucose level of 7 mmol/L and $\epsilon_r=2.1$, the simulated resonance frequency was 0.12 THz. However, when the glucose level rises after eating to 10-11 mmol/L and $\epsilon_r=2.28$, the resonance frequency shifts to 0.10 THz. Until the critical level of 20 mmol/L, the change in $\epsilon_r$ very low and hence the change in glucose level can only cause a change in transmission amplitude. The amplitude variance of the 2D SRRs require that only a change in frequency at fixed angles can be used for detection of a target molecule. However, the isotropic nature of the 3D OSRR means that at high changes in permittivity the resonance frequency can be monitored for the detection of the molecules; but even at lower changes in permittivity which cannot cause a shift in frequency, the amplitude can be also monitored since there are no other parameters that can cause it to change, thus, increasing the detection range to small changes in permittivity. As shown by the inset in FIG. 13, for the ranges of relative permittivity between 2.2-2.45 (10-20 mmol/L glucose level), the resonance frequency remains constant, however, the increase can still be monitored by measuring the change in the transmission amplitude (~6 dB). Under similar conditions the 2D array would not be able to transduce any reliable signal since the amplitude change can also be attributed to change in orientation of the structure.

The present disclosure provides a marked improvement over previous designs and techniques. The dependence of the resonance frequency of SRRs on the permittivity has been envisioned to create small scale, low power, in-vivo sensors. However, the high anisotropy of the two dimensional SRRs present a major disadvantage due to the inability for using the sensor in conditions when the orientation is difficult to control. Using the optional self-folding techniques of the present disclosure, a cubic 3D octagram based SRR with a substantially perfectly isotropic transmission response (optionally a perfectly isotropic transmission response) that is invariant under rotations about any axes. The uniformly coupled nature of the 3D OSRR provide a sensitivity that is fifty times higher than the corresponding 2D structure. The 3D OSRR demonstrates a two-fold advantage for detection of targeted molecules due to the higher sensitivity as compared to 2D coupled SRR, as well as through amplitude monitoring for permittivity changes that are too low to cause a change in resonance frequency. With optional embodiments in which the panels of the 3D microscale metamaterial sensor structures are formed of layers of GO, the structures of the present disclosure can be tuned for control over sieving and molecular absorption.

Unlike conventional SRR-based sensors that are typically in "lab-on-a-chip" or other integrated microfluidic architectures, the isotropic nature of the disclosed embodiments allow for applications other than lab-on-a-chip architecture, particularly where sensor rotation is unknown or uncontrolled. The disclosed SRRs can be used, for example, for in-vivo sensing applications. In such applications, the isotropic metamaterial can be used for in-vivo biological or chemical sensors. The small size of the sensors and its polymer composition mean the disclosed embodiments can also be made biocompatible with minimal modifications. The small scale biocompatible sensor can be implanted subcutaneously for in-vivo measurement of biological species. In addition, one application for subcutaneous sensors is for continuous glucose monitoring. An in-vivo sensor must be biocompatible and small, to minimize patient discomfort. The sensor must also be inexpensive and replaceable, as these sensors will often degrade in performance as a layer of scar tissue grows over the sensor surface. This disclosed embodiments would be considered an optical biosensor that is any sensor which uses changes in the sensor in response to light when exposed to an analyte. In addition, the disclosed SRRs can be used for in-situ chemical sensing. The isotropic sensor can also be used for in-situ measurement of chemicals present in any liquid. Yet another application for the disclosed embodiments is a meat quality assessment sensor. In this application, SRR sensors asses aging of meat products based on moisture loss. In additional applications, the disclosed embodiments can be utilized in antennas for wireless devices for telecommunications.

Although the present disclosure has been described with reference to preferred embodiments, workers skilled in the art will recognize that changes can be made in form and detail without departing from the spirit and scope of the present disclosure.

What is claimed is:

1. A three-dimensional microscale metamaterial structure comprising:
    a polygonal structure comprising at least a first panel and a second panel, wherein an edge of the first panel is connected to an edge of the second panel at a first structure corner; and
    a metal resonator pattern provided on each of the first and second panels; and
    a joint body connecting the first and second panels at the first structure corner, the joint body formed of a non-metallic material;
    wherein the resonator pattern carried by the first panel is electromagnetically coupled to the resonator pattern carried by the second panel across a gap between the resonator patterns at the first structure corner, wherein the first structure corner, including the joint body, configured to not interfere with electromagnetic coupling between the resonator patterns of the first and second panels.

2. The metamaterial structure of claim 1, wherein the polygonal structure further comprises a third panel and a metal resonator pattern provided on the third panel, and further wherein an edge of the first panel is connected to an edge of the third panel at a second structure corner, and even further wherein the resonator pattern carried by the first panel is electromagnetically coupled to the resonator pattern carried by the third panel across a gap between the resonator patterns at the second structure corner.

3. The metamaterial structure of claim 2, wherein an edge of the second panel is connected to an edge of the third panel at a third structure corner, and further wherein the resonator pattern carried by the second panel is electromagnetically coupled to the resonator pattern carried by the third panel across a gap between the resonator patterns at the third structure corner.

4. The metamaterial structure of claim 1, wherein the polygonal structure is a cube comprising six panels, the six panels including the first and second panels.

5. The metamaterial structure of claim 4, wherein the metal resonator pattern is provided on each of the six panels.

6. The metamaterial structure of claim 5, wherein the resonator pattern is symmetrical.

7. The metamaterial structure of claim 6, wherein the resonator pattern is an X shape.

8. The metamaterial structure of claim 7, wherein the resonator patterns collectively form a three-dimensional, eight-point star shape.

9. The metamaterial structure of claim 8, wherein the metamaterial structure is a three-dimensional octagram split-ring resonator.

10. The metamaterial structure of claim 1, wherein each of the panels are formed of material transparent to light.

11. The metamaterial structure of claim 1, wherein each of the panels comprises a polymer material.

12. The metamaterial structure of claim 1, wherein each of the panels comprises at least two layers of graphene oxide.

13. The metamaterial structure of claim 1, wherein the metamaterial structure is completely isotropic.

14. The metamaterial structure of claim 1, wherein the joint body is formed of a material differing from a material of the first and second panels.

15. A three-dimensional microscale metamaterial structure comprising:
    a polygonal structure provided as a cube comprising six panels, the six panels including a first panel and a second panel, wherein an edge of the first panel is connected to an edge of the second panel at a first structure corner; and
    a symmetrical metal resonator pattern provided on each of the six panels;
    wherein the resonator pattern carried by the first panel is electromagnetically coupled to the resonator pattern carried by the second panel across a gap between the resonator patterns at the first structure corner;

and further wherein the metamaterial structure is a three-dimensional octagram split-ring resonator.

16. A method of making a three-dimensional microscale metamaterial structure, the method comprising:

forming a two-dimensional net comprising an array of microscale panels each carrying a metal resonator pattern, wherein immediately adjacent ones of the panels within the array are connected by a hinge formed of a non-metallic material; and causing the two-dimensional net to self-fold into a three-dimensional shape, including causing the hinge to self-fold.

17. The method of claim 16, wherein following the step of causing the two-dimensional net to self-fold, the three-dimensional shape is a cube.

18. The method of claim 16, wherein the step of forming the two dimensional net includes generating each of the resonator patterns to have an X shape.

19. The method of claim 16, wherein the step of forming the two dimensional net includes depositing a polymer material to generate the microscale panels.

20. The method of claim 16, wherein the step of forming the two dimensional net includes depositing at least two layers of graphene oxide to generate the microscale panels.

* * * * *